US008465512B2

(12) United States Patent  
Rosenhan

(10) Patent No.: US 8,465,512 B2  
(45) Date of Patent: *Jun. 18, 2013

(54) SAFETY SUTURE CUTTING DEVICE AND RELATED METHODS

(76) Inventor: Branden D. Rosenhan, Salt Lake City, UT (US)

( * ) Notice: Subject to any disclaimer, the term of this patent is extended or adjusted under 35 U.S.C. 154(b) by 63 days.

This patent is subject to a terminal disclaimer.

(21) Appl. No.: 13/080,367

(22) Filed: Apr. 5, 2011

(65) Prior Publication Data

US 2012/0259352 A1 Oct. 11, 2012

(51) Int. Cl.  
*A61B 17/32* (2006.01)

(52) U.S. Cl.  
USPC ............................................................ 606/167

(58) Field of Classification Search  
USPC ................... 606/167, 170, 172, 148; 30/151, 30/162, 286  
See application file for complete search history.

(56) References Cited

U.S. PATENT DOCUMENTS

| 117,588 | A | | 8/1871 | Woods |
| 256,629 | A | | 4/1882 | Boman |
| 3,484,940 | A | | 12/1969 | Zell |
| 3,699,654 | A | | 10/1972 | Gerling |
| 4,242,795 | A | * | 1/1981 | Rollband et al. ................. 30/162 |
| 4,423,729 | A | | 1/1984 | Gray |
| 5,015,252 | A | | 5/1991 | Jones |
| 5,630,242 | A | | 5/1997 | Oginaezawa |
| 5,860,993 | A | | 1/1999 | Thompson et al. |
| 6,254,620 | B1 | * | 7/2001 | Koh et al. ..................... 606/167 |
| 6,446,340 | B1 | | 9/2002 | Ping |
| 6,938,345 | B2 | | 9/2005 | Yu |
| 8,181,352 | B1 | | 5/2012 | Shackelford |
| 2004/0254598 | A1 | | 12/2004 | Schumacher et al. |
| 2005/0150115 | A1 | | 7/2005 | Hanna |
| 2005/0234481 | A1 | | 10/2005 | Waller |
| 2006/0241665 | A1 | | 10/2006 | Bosley et al. |
| 2008/0271323 | A1 | | 11/2008 | Perlmutter |
| 2009/0157110 | A1 | | 6/2009 | Muto et al. |
| 2010/0234865 | A1 | | 9/2010 | Lafauci et al. |

FOREIGN PATENT DOCUMENTS

DE 4240532 3/1994

* cited by examiner

*Primary Examiner* — Ryan Severson  
(74) *Attorney, Agent, or Firm* — Workman Nydegger

(57) ABSTRACT

A sheath for use with a scalpel cutting device including a sheath body configured to cover a scalpel blade at a distal end of a scalpel cutting device. The sheath advantageously may include a plurality of slots formed therein. Providing two or more slots provides additional functionality and/or ease of manufacturing. A single sheath configuration including a plurality of slots (e.g., two) may be manufactured so as to be used with scalpels including somewhat different blade configurations (e.g., which may require a slightly different slot location). Such a universal sheath allows a single sheath design to be used with multiple scalpels, easing manufacture and reducing costs. In addition, depending on the particular location of the slots and the configuration of the scalpel blade, the different slots may each intersect the scalpel blade and provide different characteristics for cutting a suture.

15 Claims, 10 Drawing Sheets

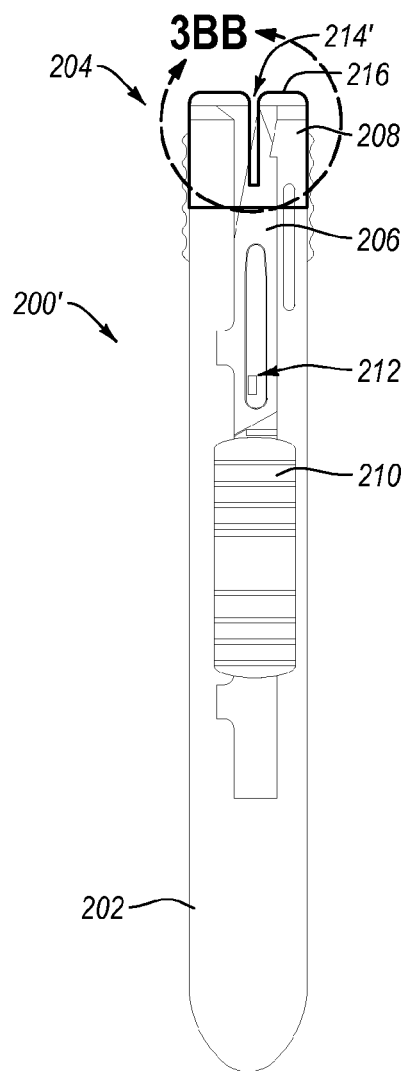
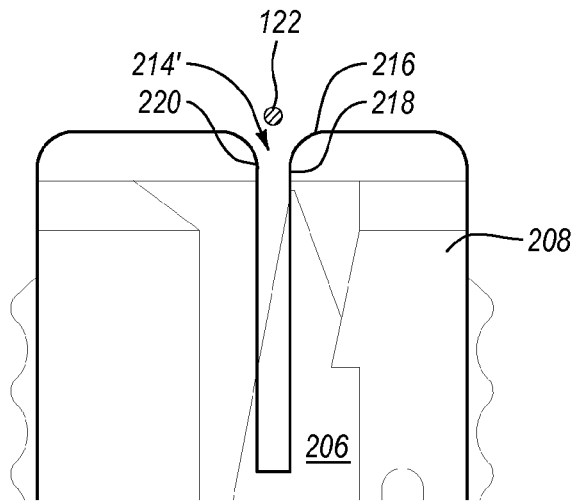
Fig. 3BB
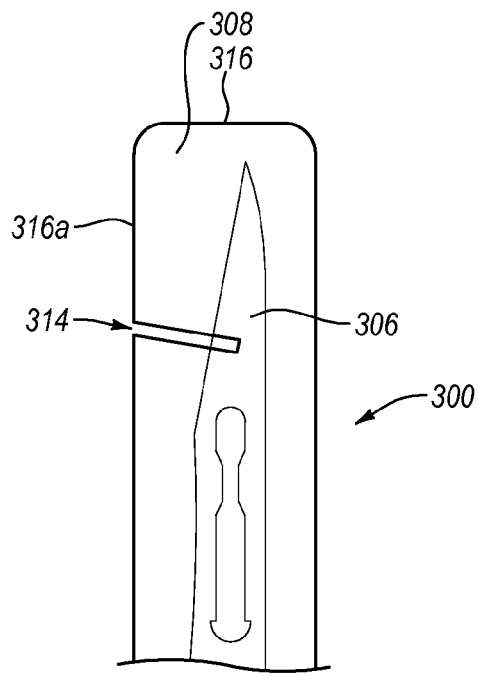
Fig. 3B
Fig. 4

SAFETY SUTURE CUTTING DEVICE AND RELATED METHODS

BACKGROUND OF THE INVENTION

1. The Field of the Invention

The present invention is in the field of medical devices, for example scalpels and other surgical cutting devices.

2. The Relevant Technology

Medical practitioners often close a wound or opening within a patient (e.g., during surgery) with sutures. Scalpels are often used as needed in performing the surgery, and then are often used for cutting the ends of sutures employed to close up the wound or opening within the patient's tissue. Depending on the nature of the procedure, sutures can be placed adjacent to a main artery or vein, and as such, any misplacement of the scalpel when cutting the suture (e.g., caused by an accidental sneeze, cough, or otherwise) could potentially be disastrous. As an alternative, it is possible to cut the sutures with scissors, but this requires an additional step and can be something of a nuisance to the practitioner, as the practitioner already has a scalpel handy.

Many scalpels include a safety sheath that covers the blade end of the scalpel. In order to use the blade (e.g., for cutting tissue or a suture) the sheath must be retracted or removed, or a retractable blade must be extended beyond the sheath, so as to expose the blade for use.

Some efforts have been made to provide an ability to access the scalpel blade for cutting a suture while the blade is safely sheathed so as to prevent accidental cuts to the patient and/or practitoner. One such configuration is shown in U.S. Patent Application 2009/0157110, which includes a notch opening 17 in the side of the sheath 18 to allow a suture to be cut without exposing blade 20. As the suture is inserted into notch opening 17, tension between the suture and the blade 20 is used to cut the suture.

Another configuration is shown in FIG. 1B, which is taken from U.S. Patent Application 2005/0234481, and which discloses a dedicated suture cutting device in which the blade 115 is somewhat protected within an alcove at the distal end of the device. Similar to the device shown in FIG. 1A, the suture is pulled tight against the blade and tension between the blade and suture cuts the suture. Such a device is not capable of performing the traditional functions of a scalpel.

Although suture-cutting devices have been proposed, there still exists a need for improved configurations that effectively sheath the blade from accidental exposure, while providing easy, fast, and efficient cutting of a suture.

SUMMARY OF THE INVENTION

The present invention is directed to a sheath for use with a scalpel cutting tool, as well as scalpel cutting tools including such sheaths. In one embodiment, the device includes a sheath body configured to cover a scalpel blade at a distal end of a scalpel cutting device. The sheath body includes a suture guide slot formed into a surface of the body, and the slot extends from a first end at the edge of the sheath body to a second end adjacent the scalpel blade so that the slot intersects the blade, and the blade is exposed within the slot (i.e., at the second end or "bottom" of the slot), but is otherwise protected by the sheath. The slot includes a width defined by first and second opposed guiding side walls, and the blade is non-perpendicular relative to the slot. The angle between the first side wall of the slot and the scalpel blade at their point of intersection is advantageously greater than 105° and less than 180°.

In the case where the first and second side walls of the suture guide slot are parallel and the blade is straight, the angle between the second side wall and the blade at their point of intersection will be equal or approximately equal to 180° minus the angle between the first side wall and the blade at their point of intersection (i.e., the two angles can sum to 180°). Generally speaking, the side wall with the largest angle relative to the blade will have the shortest length, and vice-versa. In the case where the side walls are not parallel (e.g., they converge toward the blade) and/or the blade is not straight but curved, the sum of the two angles may not be 180°. Nevertheless, in general, when the first angle is obtuse (i.e., greater than)90° the second angle will typically be acute (i.e., less than 90°).

In this embodiment, the slot walls and blade do not intersect one another in a substantially perpendicular configuration, but a more gradual angle of intersection is provided. This is advantageous as the cutting of the suture thus does not rely only on the tension between a suture that is perpendicular to the blade, and which is then pulled through the blade. Rather, the angle is significantly greater than 90° and the suture is pulled in a direction having a major component of motion that is parallel to the blade, while under slight tension, and with a minor component of motion that is perpendicular to the blade. This introduces a slicing action and allows the suture to be cut with considerably less force than is required when attempting to simply pull the suture through the blade where the orientation of the suture and blade are perpendicular relative to one another, and in which the applied force is largely perpendicular to the blade.

Such slicing or shearing action requires significantly less force to cut the suture because the component of motion or force that is perpendicular to the blade is reduced compared to when the angle is 90°. In other words, the suture motion has a significant component of motion that is parallel to the blade as the suture is pulled along the length of the blade within the slot. The interaction of the slot and suture causes the blade to progressively slice through the suture from the side, rather than there being no substantial movement of the suture along the blade length as is the case when the pulling or cutting force is perpendicular to the blade surface.

According to another embodiment, the device comprises a sheath body and a slot formed in the sheath body that intersects the scalpel blade so that the scalpel blade is exposed only within the slot, and in which the ratio of the length of the shortest slot side wall to the slot width is at least 2, more preferably at least about 3, and most preferably at least about 4. Such a ratio of slot depth to width is advantageous as it provides a greater safety factor to a user so as to keep the sharp blade well recessed and protected within the sheath compared to shallower a slot, and minimizes the tendency of the suture to be accidentally withdrawn from the slot as a result of inadvertently jerking or side-to-side movement of the suture. Such a ratio is independent of the suture diameter. For example, a larger diameter suture may benefit from a greater slot depth, as well as a greater slot width. When employed with a suture of typical diameter (e.g., about 0.1 to about 0.25 mm), the length of the shortest slot side wall may be at least 3 mm, more preferably at least about 4 mm, and more preferably at least about 5 mm from the first slot end at the edge of the sheath to where the slot intersects with the blade. In addition to better retaining the suture within the slot, such ratios and slot depths are particularly beneficial in keeping the sharp blade well away from the exterior end or side of the sheath so as to prevent accidental cuts.

The sheath may be separate and removable from the scalpel cutting tool, in which case the sheath is configured to be positioned over the distal blade end of the scalpel. In other embodiments, the sheath may be attached to the scalpel cutting tool so as to not be removable therefrom, but in which either the blade or sheath may be retracted, selectively exposing the blade.

An advantage of embodiments that include a suture guide slot at the forward end of a relatively narrow sheath is that the device can be maneuvered longitudinally to cut sutures in restricted spaces. The space in which such devices can cut may be limited only by the width of the sheath. This is in contrast to suture scissors, which often require much greater space to operate properly, or a suture cutting blade with the suture guide slot positioned on the side and that must be moved laterally (e.g., perpendicular to the longitudinal axis of the device) rather than longitudinally when cutting.

In some embodiments, the sheath may include spacing means for providing a desired blade height or distance from the skin or tissue surface. This can provide several desired functions, including leaving a suture end with a desired length and/or preventing inadvertent cutting of the suture knot, which should be positioned between the blade and the patient's tissue surface. An example of spacing means includes one or more rails or protrusions on a side of the sheath. The sheath can optionally include differently sized rails or protrusions on opposite sides of the sheath that maintain the cutting blade at different distances from the tissue surface to provide a practitioner with the ability to cut at different heights or distances from the skin depending on which side of the sheath is positioned next to the tissue surface.

In one embodiment the sheath includes a plurality of slots formed in the sheath. Such a configuration provides additional functionality and/or ease of manufacturing. For example, a single sheath configuration including a plurality of slots (e.g., two) may be manufactured so as to be used with scalpels including somewhat different blade configurations (e.g., which may require a slightly different slot location). Such a universal sheath allows a single sheath design to be used with multiple scalpels, easing manufacture and reducing costs. In addition, depending on the particular location of the slots and the configuration of the scalpel blade, the different slots may each intersect the scalpel blade and provide different characteristics for cutting a suture. For example, one slot may intersect the blade at a relatively shallow angle, providing the shearing benefits described herein, while another slot may intersect the blade at a less shallow angle nearer 90°, which may still be suitable for cutting relatively thin, low strength sutures.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. The drawings depict only typical embodiments of the invention and are not therefore to be considered limiting of its scope.

FIG. 2AA is a close up view of the slot and sheath of FIG. 2A;

FIG. 2BB is a close up view of the slot and sheath of FIG. 2B;

FIG. 3AA is a close up view of the slot and sheath of FIG. 3A;

FIG. 3B is a front side view of another scalpel including a protective sheath having a slot formed in a distal end surface thereof according to the present invention;

FIG. 3BB is a close up view of the slot and sheath of FIG. 3B;

FIG. 4 is a front side view of the distal end of another scalpel including a protective sheath having a slot formed in a side surface thereof according to another embodiment of the present invention;

FIGS. 8A and 8B are front side views of an exemplary sheath including a plurality of slots for use with different types of scalpel blades.

DETAILED DESCRIPTION OF THE PREFERRED EMBODIMENTS

I. Introduction

In one embodiment, the present invention is directed to a sheath for use with a scalpel cutting device including a sheath body configured to cover a scalpel blade at a distal end of a scalpel cutting device. The sheath advantageously includes a slot formed therein that extends from a first end at an edge of the sheath body to a second end adjacent the scalpel blade so that the slot intersects the blade and the blade is exposed only within the second end of the slot. The blade surface is non-perpendicular relative to the slot side walls, such that generally one side wall will be shorter than the other. The slot is further advantageously configured such that an angle between the first guiding side wall (e.g., the shorter side wall) of the slot and the scalpel blade at the point of intersection is greater than 105° and less than 180°. Where the slot side walls are parallel and the blade is straight, the angle between the second side wall and the blade at intersection will be supplementary to the first angle. Although the angles may not sum to 180° in embodiments including non-parallel slot side walls and/or curved blades, in general when the first angle is obtuse, the second angle will be acute.

In any case, the configuration advantageously allows a suture inserted within the slot to be sheared or sliced as the suture is pulled along the blade edge rather than simply pulled perpendicularly through the blade. Slicing the suture in this manner greatly decreases overall applied force, and particularly the component of the force applied in a direction perpendicular to the blade, which eases cutting of the suture, while also minimizing or preventing any tendency of the suture to tear through the patient's tissue as a result of the applied forces.

In another embodiment, the slot of the sheath is specifically configured to include a ratio of the length of the shortest slot side wall to the slot width that is at least 2. Such a ratio minimizes or prevents the tendency of the suture to accidentally become dislodged from the slot as a result of inadvertent movement. Such a ratio also provides sufficient slot depth to prevent accidental cuts caused by a blade which is disposed closer to the edge of the protective sheath. Even greater ratios of slot side wall length to slot width (e.g., at least about 3 or at least about 4) are even more effective at retaining the suture within the slot and preventing accidental cuts.

II. Exemplary Safety Suture Cutting Devices

Figure 2A:
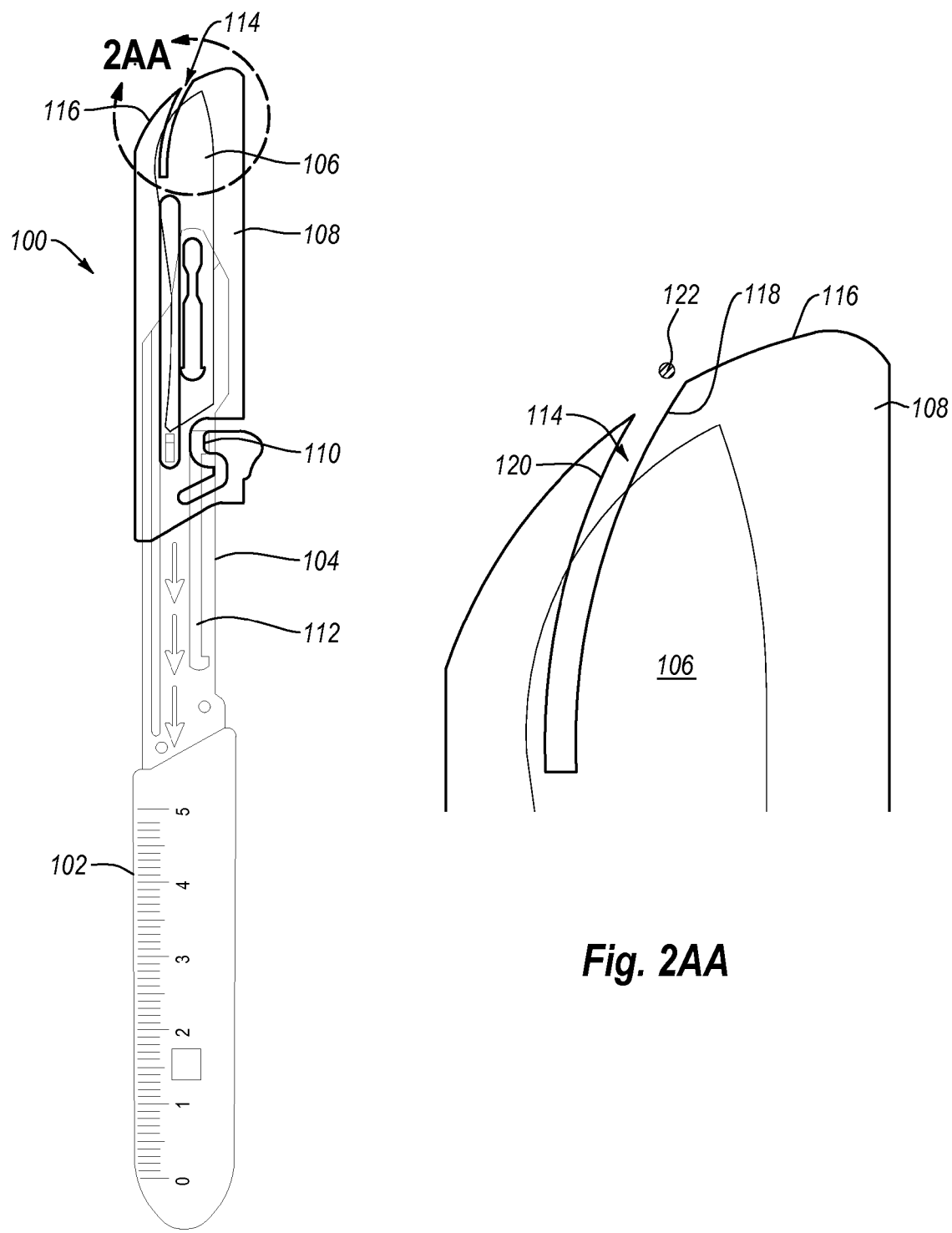
FIG. 2A is a front side view of an exemplary scalpel including a protective sheath having a slot formed in a distal end surface thereof according to the present invention.

FIG. 2A shows an exemplary scalpel 100 including a proximal gripping end 102 and a distal end 104 to which is attached a blade 106. A retractable sheath 108 is coupled over the distal end 104 so as to selectively cover and uncover blade 106. In the illustrated configuration, sheath 108 is fully extended, so as to fully cover blade 106. Retractable sheath 108 includes a tab 110 that rides within a guide slot 112 that allows the sheath to be selectively slid from the sheathed configuration shown to a configuration (not shown) in which blade 106 is exposed, extending through the distal end of sheath 108. Although one configuration of the retraction mechanism is shown, it will be understood that other retraction mechanisms may be employed. For example, in an alternative embodiment, it may be the blade that is retractable within a protective sheath (see FIGS. 3A-3B). In another embodiment, neither the sheath nor the blade may be retractable, but the sheath may be separate and removable from the scalpel. Such a removable sheath may simply be coupled or otherwise disposed over the blade so as to cover and protect the blade from accidental contact with another surface.

Figure 2B:
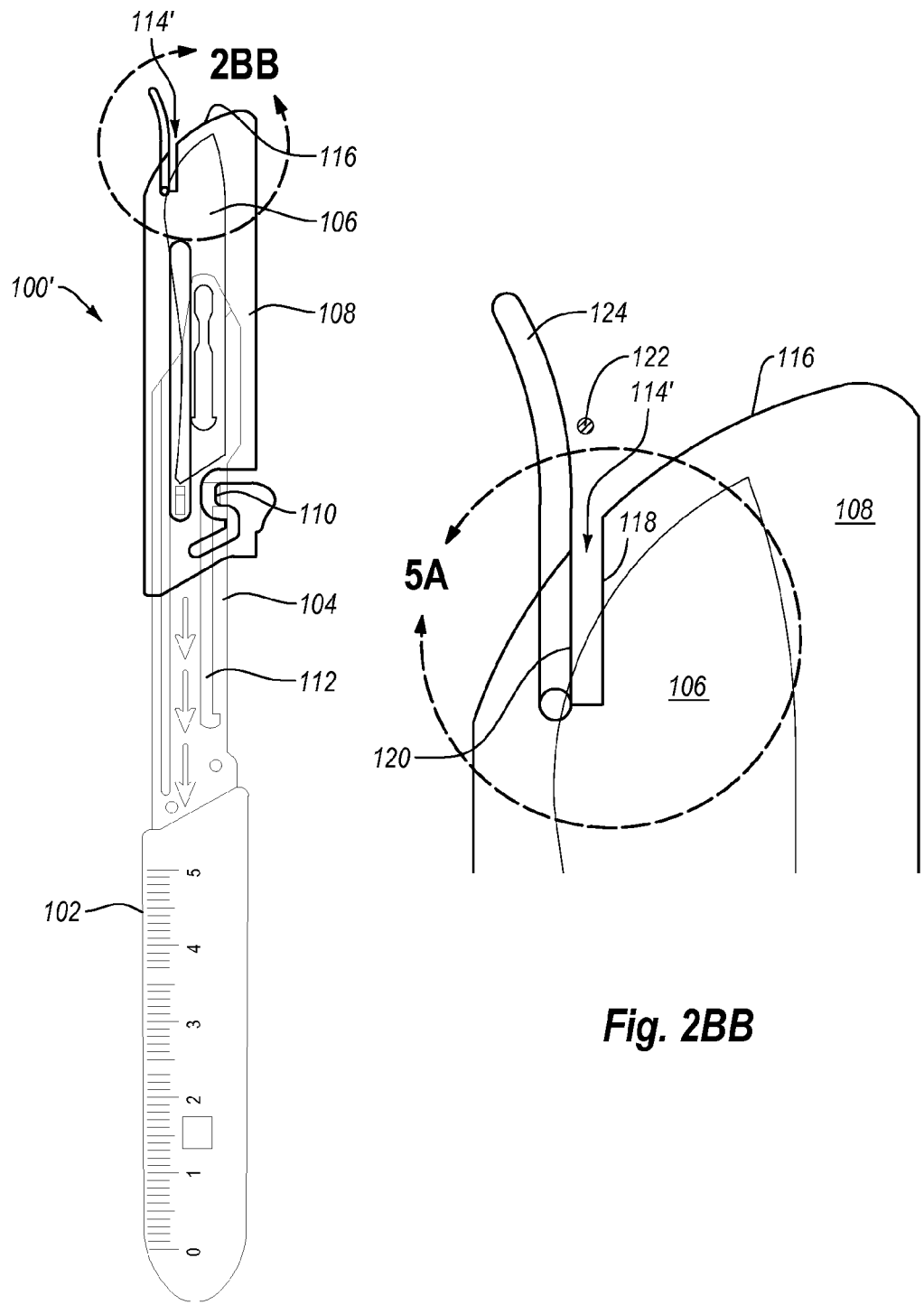
FIG. 2B is a front side view of an alternative scalpel including a protective sheath having a slot formed in a distal end surface thereof according to the present invention.

Sheath 108 includes a slot 114 formed therein. In the illustrated example, slot 114 extends from the distal end surface 116 of sheath 108 towards the sharp cutting surface of blade 106. Slot 114 intersects blade 106, as shown perhaps most clearly in FIG. 2AA. Slot 114 is shown in FIGS. 2A-2AA as being curved, while a straight slot is shown in FIGS. 2B-2BB. Slot 114 includes a first side wall 118 that acts as a guide surface on one side of slot 114 and a second side wall 120 that acts as another guide surface on the other side of slot 114. The width of the slot 114 is defined between side walls 118 and 120.

As seen in FIG. 2AA, a suture 122 can be introduced into slot 114 in preparation for easily and efficiently cutting the suture. For example, suture 122 may be guided downward along side wall 118 until it reaches the intersection of side wall 118 with blade 106. Because blade 106 advantageously forms an angle relative to side wall 118 that is greater than 90° and the slot 114 is sufficiently wide relative to the suture diameter, the suture 122 may be pulled across blade 106 towards opposite side wall 120, slicing through suture 122 with relatively little downward force applied. In other words, only a minor component of the applied force is directed perpendicular to the blade 106, while the major component or vector of the applied force is directed parallel to the blade 106. As a result of such a slicing action and configuration, the forces transmitted upwards through the suture to the patient's tissue are minimized. By comparison, when applying a force that is entirely (or nearly so) perpendicular to the blade without any substantial translation of the suture along the blade surface, not only is the magnitude of the component of the applied force that is perpendicular to the blade significantly greater, but the overall magnitude of the applied force must also be greater than that applied in the inventive embodiments. Such higher forces increase the tendency to tear the suture through the patient's flesh.

For example, before cutting, the opposite end of the suture may be stitched into the patient's tissue. As a result, it is desirable to minimize pulling forces on the suture that might otherwise pull the suture, cutting through the patient's tissue (e.g., similar to a cheese wire). The described configurations provide slot to blade angles and slot widths that are configured so as to minimize such tissue cutting forces. Preferably, the angle between the side wall 118 of the slot and the blade 106 is between about 130° and about 170°, more preferably between about 150° and about 170°. For example, the configuration shown in FIG. 2AA includes an angle of about 160° between side wall 118 and blade 106.

It will be appreciated that the angle formed between second side wall 120 of the slot and the blade will be supplementary to the above described angles where the side walls 118 and 120 are parallel and the blade is substantially straight within the slot 114. Although in embodiments including non-parallel side walls and/or blades exhibiting substantial curvature within the exposed portion of the slot the two angles may not sum to 180°, in general the angle associated with the shorter side wall will be obtuse, while the angle associated with the longer side wall will be acute.

The described configuration that introduces a slicing action when cutting the suture is particularly beneficial for use with strong, difficult to cut sutures. For example, some polymeric sutures are so strong that they are difficult if not impossible as a practical matter to cut by simply pulling the suture perpendicularly through a blade without tearing the just completed stitched portion of the suture through the patient's flesh. The particular slot to blade angle provided, as well as the blade length exposed within the slot selected may depend on the strength of sutures to be cut with the device. For example, stronger sutures may require a shallower angle (i.e., closer to 180°) and/or a greater ratio of exposed blade length to suture diameter. Relatively weaker sutures may be sliced without any cheese-wire effect of tearing through the patient's flesh with a sharper angle (i.e., closer to 105°) and/or a lower ratio of exposed blade length to suture diameter.

Figure 5A:
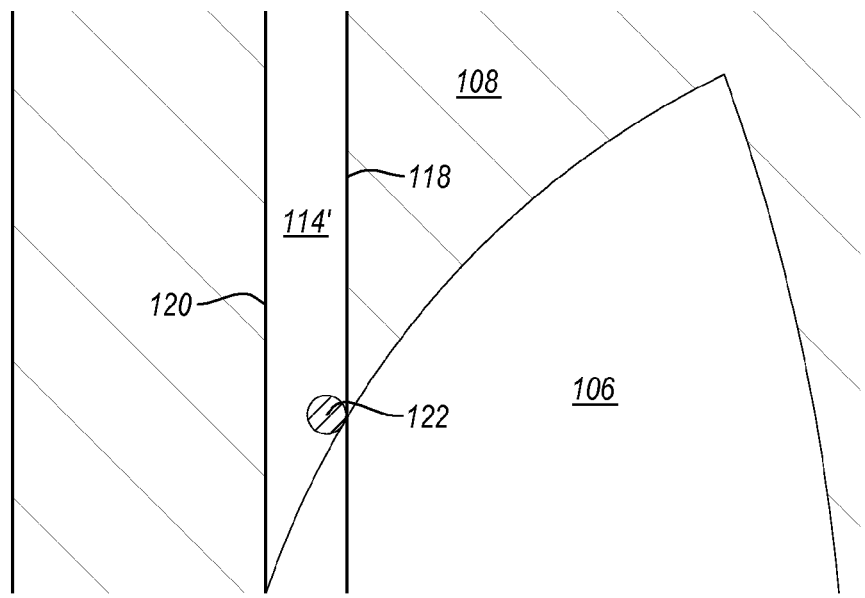
FIG. 5A is a partial cross-sectional view showing the distal end of a scalpel blade and sheath slot similar to that of FIG. 2BB in which a suture to be cut is positioned at the intersection of the slot and blade.
Figure 5B:
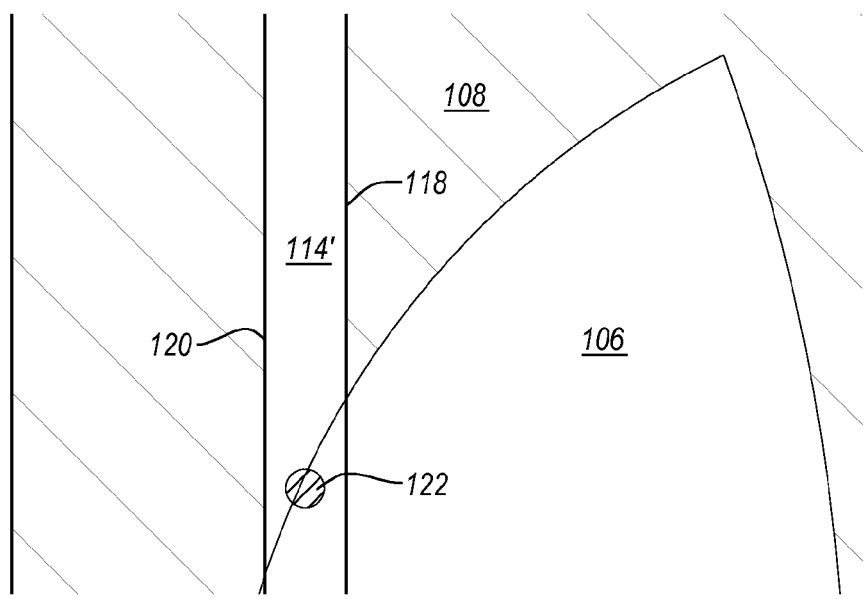
FIG. 5B is a partial cross-sectional view similar to that shown in FIG. 5A in which the suture has advanced along the exposed blade surface, slicing into the suture.

It is also noted that the width of slot 114 is significantly greater than the diameter or thickness of the suture 122 to be cut. The term "diameter" will be used hereinafter, although it will be understood that the suture may have a cross-section that is other than round, in which the diameter referred to is the suture thickness. This width of the slot 114 provides sufficient space for the suture to be pulled along the blade 106 while a small downward force component is applied so that the blade slices into the suture as it is pulled along blade 106. FIGS. 5A-5B, described in further detail below, show such a progressive slicing action. For example, the width of slot 114 may be such so as to provide a length of exposed blade 106 within slot 114 that is at least about 1.5 times the diameter of the suture 122 to be cut. In one embodiment, the exposed blade length within slot 114 may be at least about 2 times the suture diameter; in another embodiment the exposed blade length may be between about 4 times and about 12 times the suture diameter. For example, the arc length of blade 106 illustrated in FIG. 2AA is about 6 times the diameter of suture 122. The width of slot 114 should not be so great as to allow inadvertent cutting of a practitioner's finger or other appendage.

FIGS. 2B-2BB illustrate another embodiment of a scalpel 100' that is similar to that shown in FIGS. 2A-2AA, but in which the slot 114' is substantially straight rather than curved. In addition, scalpel 100' further includes a guide member 124 disposed adjacent slot 114' that extends beyond the distal mouth of slot 114', adjacent sidewall 120 so as to aid in guiding suture 122 into slot 114'. Such a guide member is beneficial in helping to introduce the suture into slot 114' (e.g., by placing suture 122 in contact with guide 124 and then pulling suture 122 downward, where it is guided into slot 114'). Guide member 124 may alternatively be positioned adjacent guiding side wall 118. Such a guide member may be provided with any of the embodiments described herein.

In addition, the mouth of slot 114' is shown as being flared in embodiment 100', while that of FIGS. 2A-2AA is not flared. Although both slots 114 and 114' are shown as having a substantially constant width over substantially the entire depth of the slot, it will be understood that alternative embodiments may include non-parallel side walls so that the width varies. For example, one embodiment may include side walls that converge towards the blade, which facilitates easier introduction of the suture into the slot. In another example, an embodiment may include a mouth of a given width, which widens as the slot approaches the blade 106. Such a configuration may be beneficial in helping to prevent accidental release of the suture 122 after entrance into the slot, while also providing the desired ratio of exposed blade length to suture diameter where the slicing occurs (i.e., at the blade edge). Where the width of the slot varies, the sidewalls may be smooth or may include an abrupt transition, as desired.

Figure 3A:
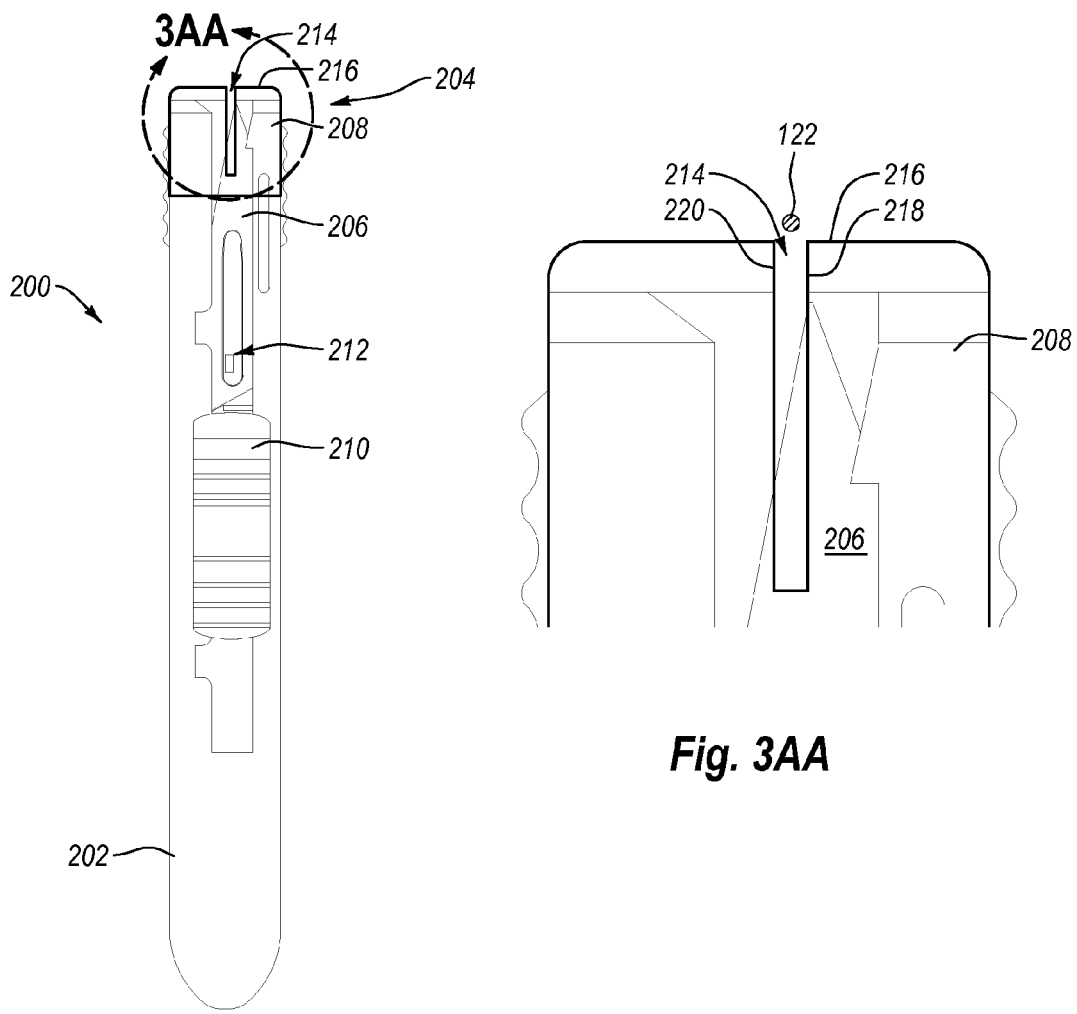
FIG. 3A is a front side view of another scalpel including a protective sheath having a slot formed in a distal end surface thereof according to the present invention.

FIGS. 3A-3AA illustrate another embodiment of a scalpel 200 including a proximal gripping end 202 and a distal end 204 within which is disposed a blade 206. In this embodiment, it is the blade 206 that is extendable beyond and retractable within the distal end 204 of the scalpel 200. Distal end 204 includes a sheath 208 within which blade 206 may be selectively retracted and protected. Retractable blade 206 may be attached to a slidable member 210 that rides within a guiding slot 212 that allows the blade 206 to be selectively slid from the sheathed configuration (shown) to a configuration in which blade 206 extends beyond distal end 216 of sheath 208. It will be understood that other retraction mechanisms may be employed, or that the sheath may be separate and removable from the scalpel cutting tool.

Similar to the above described embodiments, sheath 208 includes a slot 214 formed therein. In the illustrated example, slot 214 extends from the distal end surface 216 of sheath 208 towards blade 206. Slot 214 intersects blade 206, as shown perhaps most clearly in FIG. 3AA. Slot 214 is shown in FIGS. 3A-3AA as being substantially straight and vertical (i.e., parallel to a longitudinal axis of the scalpel 200), rather than curved as shown in FIGS. 2A-2AA. Slot 214 includes a first side wall 218 that acts as a guide surface on one side of slot 214 and a parallel second side wall 220 that acts as another guide surface on the opposite side of slot 214. The width of the slot 214 is defined between side walls 218 and 220. Another difference of scalpel 200 is that blade 206 is shown as having a substantially straight cutting edge, rather than the curved cutting edge shown in FIGS. 2A-2BB. In addition, the distal end 216 of sheath 208 is illustrated as flat (i.e., perpendicular to a longitudinal axis of the scalpel), rather than including a curved distal end surface as the embodiments of FIGS. 2A-2BB. It will be understood that various sheath and blade configurations may be used within any given embodiment. For example, one embodiment (not shown) may include a straight edged blade as in FIG. 3A-3BB with a curved end sheath as in FIG. 2A-2BB.

FIGS. 3B-3BB illustrate another embodiment of a scalpel 200' similar to that of FIG. 3A-3AA, but in which the mouth of slot 214' is flared rather than square, as is the mouth of slot 214. Flaring may aid a user in introducing the suture 122 into the slot.

Table I below shows shorter side wall to blade edge angle information (Angle), exposed blade length to suture diameter ratios (Ratio 1), and shorter side wall length to slot width ratios (Ratio 2) for the embodiments shown in FIGS. 2AA, 2BB, 3AA, 3BB, and FIG. 4.

TABLE I

| Example | Angle | Ratio 1 | Ratio 2 |
| --- | --- | --- | --- |
| FIG. 2AA | 158° | 6.1 | 3.8 |
| FIG. 2BB | 149° | 4.8 | 2.9 |
| FIG. 3AA | 169° | 10.9 | 2.4 |
| FIG. 3BB | 169° | 10.9 | 2.4 |
| FIG. 4 | 90° | 2.0 | 6.5 |

FIG. 4 illustrates another alternative embodiment. As will be readily appreciated, in this embodiment, both the side walls of slot 314 form an angle relative to the blade 306 that is less than 105° (e.g., about 90° for each), and the slot 314 is formed into a lateral side 316a, rather than the distal end 316 of sheath 308. As such, this embodiment may be less preferred for reasons described above relative to the preferred angles that are greater than 90° and the associated slicing action achieved, but this embodiment illustrates other desirable features that may be incorporated into the inventive devices.

Figure 1A:
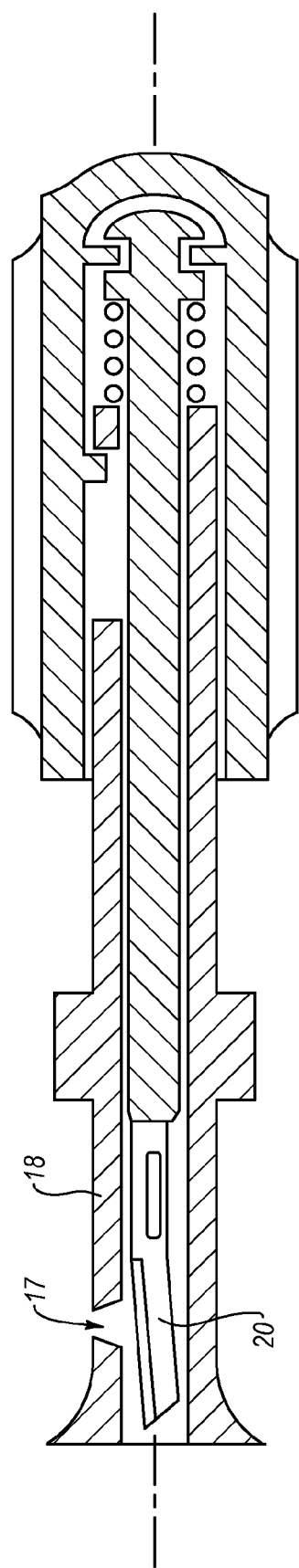
FIG. 1A is cross-sectional view through a prior art scalpel including a notch for cutting a suture.
Figure 1B:
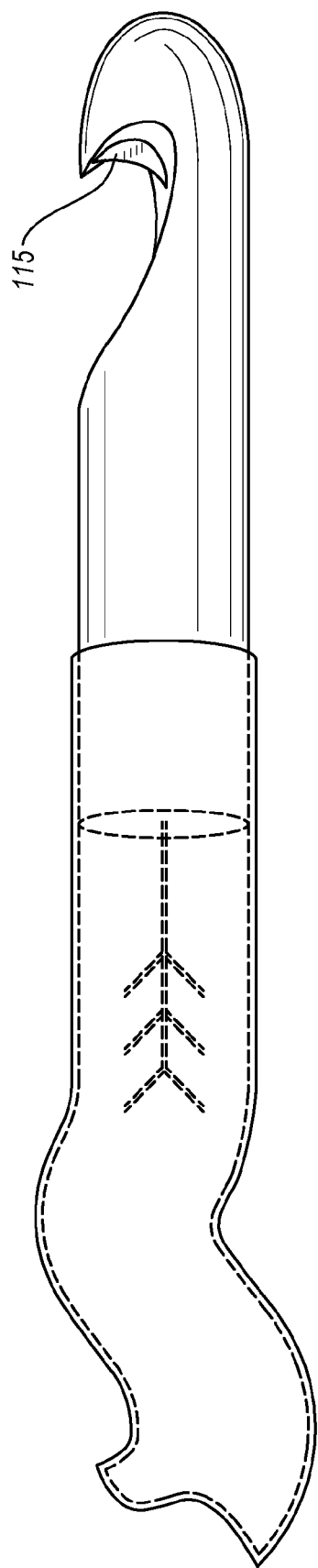
FIG. 1B is a perspective view of a prior art dedicated suture cutting device.

For example, scalpel 300 includes a slot 314 having a ratio of the length of the shortest side wall of slot 314 to slot width that is at least 2, more preferably at least about 3. In some embodiments, the ratio may be even greater (e.g., at least about 4). Such a ratio is independent of the suture diameter to be cut. Such a configuration provides an additional degree of safety over the prior art embodiment shown in FIG. 1A, in which the slot appears wide and short rather than exhibiting the greater ratios herein described. In such embodiments, the higher ratio of side wall length to slot width aids in retaining the suture within the slot 314 once introduced. With a shallower slot, the suture may easily become dislodged from the slot, leading to frustration and wasting the time of the practitioner. In addition, shallow and wide slots may position the blade dangerously close to the notch formed in the side of the sheath.

When used with typically sized sutures (e.g., about 0.1 mm to about 0.25 mm in diameter), the length of the shortest side wall may be at least 3 mm, more preferably at least about 4 mm, and even more preferably at least about 5 mm. Even greater lengths are possible (e.g., 8 mm or 10 mm). Of course, ratios of shortest side wall to slot width of at least 2, at least 3, at least 4 and slot depths of at least 3 mm, 4 mm, 5 mm or more as described above may be included within the embodiments illustrated and described above in conjunction with FIGS. 2A-3BB, which configurations may be particularly preferred as providing collectively the most benefits. In addition, the slots of any of the embodiments shown in FIGS. 2A-3BB may be formed into a lateral side, rather than the distal end of the sheath.

FIG. 5A illustrates a further close up view similar to the scalpel embodiment shown in FIG. 2BB, in which the suture 122 is positioned at the intersection of guiding side wall 118 and blade 106. As shown in FIG. 5B, as the suture is pulled along the edge of blade 106, blade 106 slices into the side of suture 122. The applied force includes a minor component that is in a direction perpendicular to the blade surface and a major component that is in a direction parallel to the blade surface. For example, as seen in FIG. 5B the suture 122 has advanced about half way along the length of the exposed blade edge, slicing nearly completely through suture 122. Suture 122 will be completely severed prior to reaching opposite guiding side wall 120. Of course, the device may be used by initially positioning the suture 122 at the intersection of side wall 120 and blade 106 and advancing along blade 106 in the opposite direction, although it may be preferred to progress "down" the blade 106, rather than "up" the blade 106.

Each of the described embodiments advantageously provides the ability to safely and efficiently cut a suture without having to extend the scalpel blade to an unprotected position in order to perform the cutting.

Figure 6:
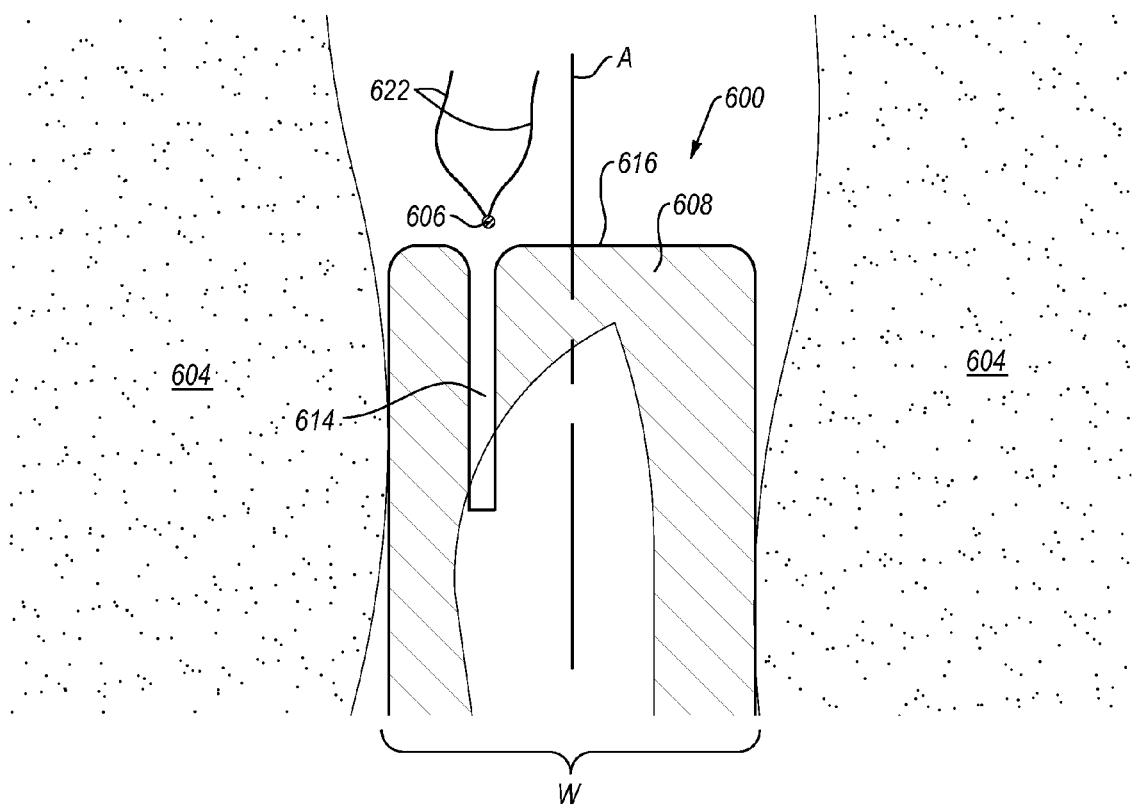
FIG. 6 illustrates how an exemplary safety suture cutting device is able to cut a suture in a restricted space.

As illustrated in FIG. 6, an advantage of embodiments that include a suture guide slot 614 at the forward end 616 of a relatively narrow sheath 608 is that the device 600 can be maneuvered longitudinally (i.e., in a direction that is generally parallel to the longitudinal axis A of the device) to cut sutures 622 in a restricted space defined by obstructions 604 on one or both sides of the suture knot 606. The space in which such devices can cut may be limited only by the width W of the sheath 608. This is in contrast to suture scissors, which often require much greater space to operate properly, or a suture cutting blade with the suture guide slot positioned on the side and that must be moved laterally (e.g., perpendicular to the longitudinal axis A of the device) rather than longitudinally when cutting. The width W can be configured to be about 1 inch (about 25 mm) or less, for example, not more than about 0.5 inch so as to allow the device to slide easily between closely spaced obstacles, cutting a suture disposed therebetween. For example, with scissors, if the practitioner were required to open the scissor blades to more than width W, then the convenience and/or effectiveness of the cutting is negatively affected. With a device including a suture guide slot positioned on the side, the practitioner may be required to orient the device and blade so as to face the patient's tissue, which can result inadvertent cuts to the patient.

Figure 7A:
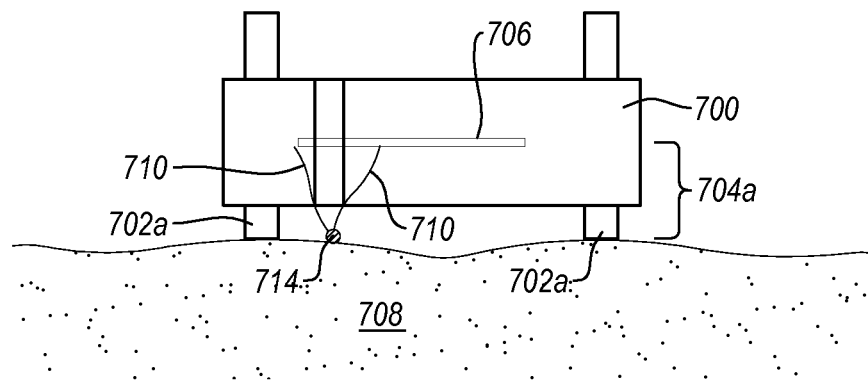
FIGS. 7A and 7B are distal end views of a sheath having rails that provide a predetermined height or distance between the suture cutting blade and the skin surface.
Figure 7B:
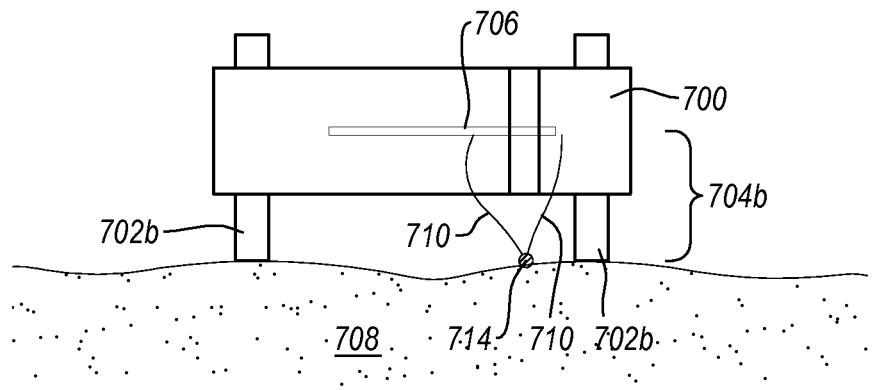

As illustrated in FIGS. 7A and 7B, the sheath 700 may include one or more spacing rails or protrusions 702a, 702b on one or both surfaces for providing a desired height or distance 704a of the cutting blade 706 from the skin or tissue surface 708. This can provide several desired functions, including leaving a suture end 710 with a desired length 704a and/or preventing inadvertent cutting of the suture knot 714, which should be positioned between the blade 706 and the patient's tissue surface 708. As shown in FIG. 7A, first spacing rails or protrusions 702a on a first side of the sheath 700 provide a first height or distance 704a of the blade 706 from the skin or tissue surface 708. As shown in FIG. 7B, second spacing rails or protrusions 702b on a second side of the sheath 700 provide a second larger height or distance 704b of the blade 706 from the skin or tissue surface 708. Thus, the distance 704a, 704b that the cutting blade 706 is maintained from the tissue surface 708 can be changed by orienting either the first side or second side of the sheath 700 adjacent to the tissue surface 708. The spacing rails or protrusions 702a, 702b comprise examples of spacing means within the scope of the invention, although other structures known in the art or described herein can provide spacing means (e.g., guide member 124 described above may protrude from the side of the sheath so as to provide spacing means).

The spacing means can advantageously be used to cut a pair of suture ends the same length to provide a cleaner, more professional look as compared to random lengths that often occur when cutting sutures using scissors or an unguided scalpel blade. In addition, the spacing means can ensure that the suture end has a desired length to prevent inadvertent slipping and untying of a suture knot, as can occur when the suture end is excessively short (e.g., less than 1 mm), particularly when using smooth polymeric sutures that have less friction and may be more prone to slippage. Even worse, without such spacing means, the practitioner may accidentally cut into the suture knot, requiring restitching of the suture. The ability to cut the suture at a predetermined distance from the tissue surface greatly facilitates the suture cutting process and eliminates guesswork and error inherent in such procedures.

For example, if the minimum suture end length required by the procedure is 3 mm but the cutting tolerance to account for surgeon error and/or limits in visibility is 3 mm, the surgeon might have to try to leave a suture end length of 6 mm to ensure that at least 3 mm of the suture remains. This can leave messy looking and/or uncomfortable suture ends. Providing a device that ensures a predetermined suture end length of 3 mm can simultaneously maximize safety, aesthetics and patient comfort with little or no effort on the part of the surgeon.

According to one embodiment, the sheath and/or spacing means can be configured to provide a desired height or distance of the blade from the tissue surface that is one or more (e.g., two) of 1 mm, 1.5 mm, 2 mm, 2.5 mm, 3 mm, 3.5 mm, 4 mm, 5 mm, 6 mm, 7 mm, 8 mm, 10 mm, or decimal increments above, below or between these exemplary distances). By way of example, the blade height or distance from the tissue surface may be 3 mm when a first side of the sheath is oriented toward the tissue surface and 5 mm when a second side of the sheath is oriented toward the tissue surface. The device also may include means for raising or lowering the height of the rails, protrusions or other spacing means in order to provide greater adjustability of the blade height or distance from the tissue surface (e.g., a ratching mechanism).

Sheath 108 includes a slot 114 formed therein. In the illustrated example, slot 114 extends from the distal end surface 116 of sheath 108 towards the sharp cutting surface of blade 106. Slot 114 intersects blade 106, as shown perhaps most clearly in FIG. 2AA. Slot 114 is shown in FIGS. 2A-2AA as being curved, while a straight slot is shown in FIGS. 2B-2BB. Slot 114 includes a first side wall 118 that acts as a guide surface on one side of slot 114 and a second side wall 120 that acts as another guide surface on the other side of slot 114. The width of the slot 114 is defined between side walls 118 and 120.

FIGS. 8A and 8B illustrate an embodiment of a safety sheath 808 including a plurality (e.g., at least two) of slots 814a and 814b. Each slot extends from distal end surface 816 of sheath 808 towards the sharp cutting surface of blade 806 or 806'. FIG. 8A shows the sheath 808 in conjunction with a curved blade 806 similar to that shown in FIGS. 2A-2AA, while FIG. 8B shows the sheath 808 in conjunction with a straight blade 806' similar to that shown in FIGS. 3A-3AA.

Providing a sheath 808 with two or more slots provides ease of manufacturing benefits (i.e., the same sheath may be employed with different scalpel configurations) so that a single sheath can be manufactured and usable for use with multiple blade configurations and/or sizes. In addition or alternatively, a sheath with multiple slots can provide additional functionality as compared to a sheath including only a single slot. Of course, any of the other sheath configurations described herein may be modified by the addition of one or more additional slots.

Providing a sheath 808 with a plurality of slots may allow the sheath 808 to be used with different scalpel configurations in which the exact location of the cutting edge of the blade may be in a somewhat different location depending on the particular scalpel configuration. Providing such a universal sheath including a plurality of slots provides a manufacturing advantage, as the same sheath configuration may be used with different scalpel blade configurations (e.g., as shown in FIGS. 8A and 8B) or sizes. For example, one of slots 814a, 814b may be located so as to provide a desired intersection with one type of scalpel blade (e.g., a curved blade such as that shown in FIG. 8A), while the other slot may be located so as to provide a desired intersection with another type of scalpel blade (e.g., a straight blade such as that shown in FIG. 8B) so as to provide the desired shearing action and/or shallow intersection between the blade and slot.

With regard to added functionality, when using a sheath 808 in conjunction with a straight blade 806' such as that shown in FIG. 8B, a practitioner may typically use first slot 814a as it may provide a desired shallow angle (e.g., greater than about 105° and less than 180°) and full extension across the slot no matter the exact retraction position of blade 806'. In other words, one of the slots may provide one angle between the side wall of the slot and the scalpel blade at an intersection of the two that is different from the angle provided between the side wall and the scalpel blade at an intersection of the two in the other slot.

When using the sheath 808 in conjunction with a curved blade 806 as shown in FIG. 8A, a practitioner may typically wish to use second slot 814b, which would provide a shallow shearing angle and a relatively long distance along which the suture may be pulled so as to cut through the suture. Of course, should a practitioner desire, the suture may be introduced into first slot 814a of the embodiment shown in FIG. 8A, particularly where the suture may be relatively easy to cut through, e.g., where the length for a shearing action and/or a more shallow intersection angle is not necessary.

Similarly, where the second slot 814b of the embodiment of FIG. 8B were to intersect blade 806', a suture may be introduced into this second slot for cutting, where desired. In some combinations of the sheath with the scalpel blade, the second slot may not provide an intersection with a particular scalpel blade, although intersection between the slot and blade is provided within at least one of the slots (e.g., typically at least first slot 814a will provide access to the scalpel blade).

Figure 8C:
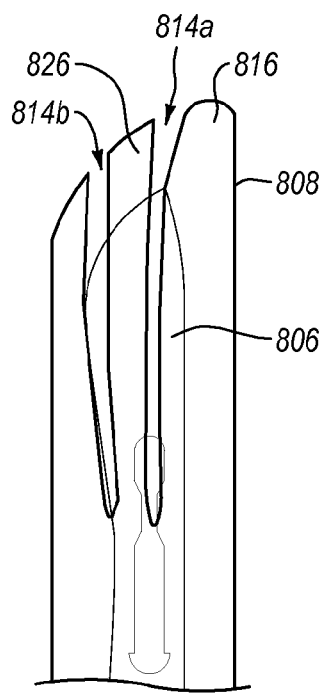
FIG. 8C is a distal end view of a sheath similar to that of FIG. 8A including rails providing a predetermined height or distance between the blade and a skin surface.
Figure 8C:
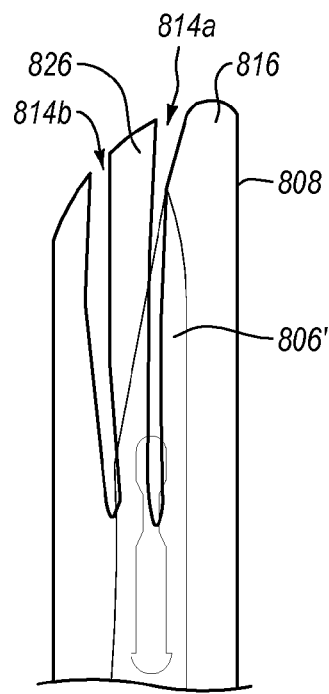
Figure 8C:
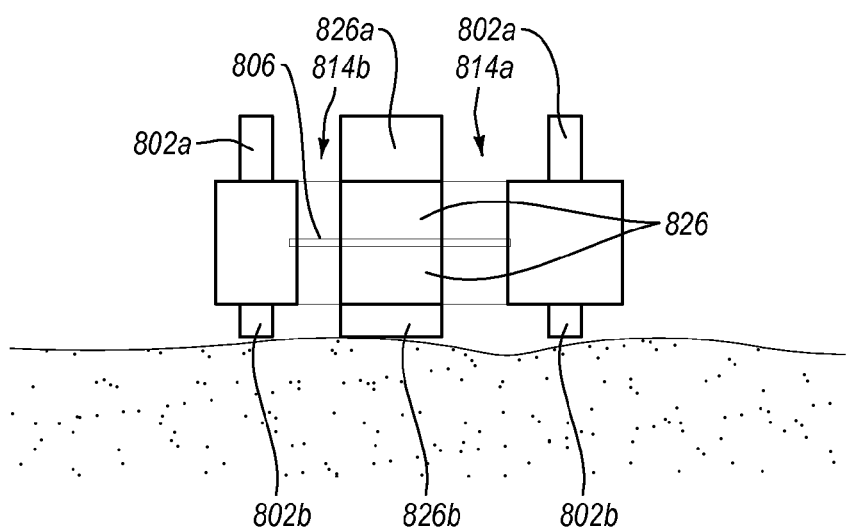

According to one embodiment and as shown in FIG. 8C, where two slots are provided, the portion of the sheath 826 may be reinforced and thickened as compared to other portions adjacent slots 814a and 814b, as this relatively narrow middle pillar portion 826 may otherwise be prone to breakage. In one embodiment, the thickening of middle pillar portion 826 may be by forming a transversely thickened rail(s) or protrusion(s) 826a, 826b at middle pillar portion 826 that extends from the top and/or bottom surface of sheath 808 so as to acts as an additional fixed length cutting rail guide in conjunction with other rails 802a and 802b (e.g., similar to rails 702a and 702b of FIGS. 7A-7B).

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope. Additionally, as used in this specification and the appended claims, the singular forms "a," "an" and "the" include plural referents unless the context clearly dictates otherwise.

What is claimed is:

1. A scalpel cutting device comprising:
a scalpel blade positioned at a distal end of an elongate portion of the scalpel cutting device, the scalpel blade having a straight cutting edge;
a sheath body configured to cover the scalpel blade in a covered position, the sheath and the blade movable between the covered position and an uncovered position in which the blade is exposed for cutting tissue through an opening in a distal end of the sheath; and
a first slot formed in the sheath body, the first slot extending between first and second surfaces of the sheath body and extending inward from an edge of the distal end of the sheath body toward the blade, wherein:
with the scalpel blade in the covered position, the first slot has a sidewall that intersects the straight cutting edge at an angle between 105° and 180° such that the first slot causes shearing of a suture sliding inward therethrough.

2. The scalpel cutting device as recited in claim 1, wherein the sheath comprises a second slot formed in the sheath body, the second slot having a sidewall that intersects the straight cutting edge at an angle between 105° and 180°.

3. The scalpel cutting device as recited in claim 2, wherein the side wall of the first slot intersects the scalpel blade at a different angle than the sidewall of the second slot.

4. The scalpel cutting device as recited in claim 1, wherein the first slot ends where the first slot intersects the straight cutting edge.

5. The scalpel cutting device as recited in claim 1, wherein the sheath further comprises spacing means for providing a desired height or distance of the scalpel blade from a skin or tissue surface.

6. The scalpel cutting device as in claim 1, wherein the sheath further comprises one or more rails or protrusions extending from a surface of the sheath for providing a desired height or distance of the scalpel blade from a skin or tissue surface.

7. The scalpel cutting device as recited in claim 1, wherein the first side wall intersects the straight cutting edge at an angle between 130° and 170°.

8. The scalpel cutting device as recited in claim 1, wherein the first side wall intersects the straight cutting edge at an angle between 150° and 170°.

9. The scalpel cutting device as in claim 1, wherein the blade height above a tissue surface in contact with the sheath is at least 1 mm.

10. The scalpel cutting device as in claim 1, wherein the blade height above a tissue surface in contact with the sheath is at least 3 mm.

11. The scalpel cutting device as in claim 1, wherein the blade height above a tissue surface in contact with the sheath is in a range from 1-10 mm.

12. The scalpel cutting device as in claim 1, wherein the blade height above a tissue surface in contact with the sheath is in a range from 2.5-7.5 mm.

13. A method for trimming a suture comprising, providing a suture cutting device as in claim 1; and drawing a suture through the slot across the straight cutting edge, thereby trimming the suture length.

14. A method as in claim 13, further comprising moving the scalpel blade to the uncovered position and back to covered position prior to drawing the suture through the slot.

15. A method as in claim 14, wherein moving the scalpel blade to the uncovered position comprises extending the blade beyond the sheath and moving the scalpel blade back to the covered position comprises retracting the blade into the sheath.

* * * * *